(12) United States Patent
Kornbluth et al.

(10) Patent No.: US 12,644,884 B2
(45) Date of Patent: Jun. 2, 2026

(54) SENSOR REFRESH SYSTEMS

(71) Applicant: Robert Bosch GmbH, Stuttgart (DE)

(72) Inventors: Mordechai Kornbluth, Brighton, MA (US); Karim Gadelrab, Boston, MA (US); Jonathan Mailoa, Cambridge, MA (US); Kaushal Sagar, Singapore (SG); Soo Kim, Cambridge, MA (US); Shilpa Pant, Singapore (SG); Lloyd Ah Qune, Singapore (SG)

(73) Assignee: Robert Bosch GmbH, Stuttgart (DE)

( * ) Notice: Subject to any disclaimer, the term of this patent is extended or adjusted under 35 U.S.C. 154(b) by 63 days.

(21) Appl. No.: 17/844,993

(22) Filed: Jun. 21, 2022

(65) Prior Publication Data

US 2022/0317118 A1     Oct. 6, 2022

Related U.S. Application Data

(62) Division of application No. 16/731,430, filed on Dec. 31, 2019, now Pat. No. 11,391,730.

(51) Int. Cl.
G01N 33/543 (2006.01)
G01N 21/64 (2006.01)

(52) U.S. Cl.
CPC ... G01N 33/54306 (2013.01); G01N 21/6428 (2013.01); *G01N 2021/6439* (2013.01)

(58) Field of Classification Search
CPC ......... G01N 33/54306; G01N 21/6428; G01N 2021/6439; G01N 33/84; G01N 21/645; G01N 2021/6432
See application file for complete search history.

(56) References Cited

U.S. PATENT DOCUMENTS 4,729,950 A * 3/1988 Kricka ................. G01N 33/535
                                                    435/7.92
5,306,644 A * 4/1994 Myerholtz ........... G01N 29/022
                                                    73/61.49
5,950,071 A * 9/1999 Hammond ........ H01L 21/02046
                                                    438/115
8,242,162 B2   8/2012 Meador et al.
8,414,831 B2   4/2013 Jayatissa
         (Continued)

FOREIGN PATENT DOCUMENTS

GB      2412657 A  * 10/2005  .......... B01J 19/0046
WO   WO-9516052 A1 *  6/1995  ............. C12Q 1/001

OTHER PUBLICATIONS

Carol Jurchenko and Khalid S. Salaita, "Lighting Up the Force: Investigating Mechanisms of Mechanotransduction Using Fluorescent Tension Probes", 2015, Molecular and Cellular Biology, 35(15) (Year: 2015).*

(Continued)

*Primary Examiner* — Henry H Nguyen
(74) *Attorney, Agent, or Firm* — Brooks Kushman P.C.

(57) ABSTRACT

A sensor refresh system. The sensor refresh system includes a sensor assembly including a sensing surface. The sensor refresh system includes a sensor attached to the sensing surface of the sensing assembly. The sensor includes a receptor binding a chemical species in a binding state. The sensor refresh system further includes an optical source irradiating the sensor when the chemical species is in the binding state to dissociate the chemical species from the receptor of the sensor in a dissociation state.

20 Claims, 1 Drawing Sheet

(56)                    References Cited

U.S. PATENT DOCUMENTS

| | | | |
|---|---|---|---|
| 10,112,169 B2 | 10/2018 | Xu et al. | |
| 2007/0042450 A1* | 2/2007 | McGimpsey | G01N 33/5438 |
| | | | 435/14 |
| 2009/0061532 A1* | 3/2009 | Papineni | G01N 33/54346 |
| | | | 436/501 |
| 2009/0211345 A1* | 8/2009 | Nahm | G01N 21/8483 |
| | | | 73/61.55 |
| 2011/0026870 A1* | 2/2011 | Sanders | G02B 6/02385 |
| | | | 385/12 |
| 2017/0107562 A1* | 4/2017 | Rothberg | C12Q 1/6874 |
| 2017/0176332 A1* | 6/2017 | Scolan | B82Y 30/00 |

OTHER PUBLICATIONS

Carter et al., "Fluorescent Sensors for Measuring Metal Ions in Living Systems", Chemical Reviews, vol. 114, No. 8, pp. 4564-4601, 2014, 38 pages.

Spinelle et al., "Review of Portable and Low-Cost Sensors for the Ambient Air Monitoring of Benzene and Other Volatile Organic Compounds", Sensors, doi:10.3390/s17071520, Jun. 28, 2017, 30 pages.

He et al., "A fluorescent chemosensor for sodium based on photoinduced electron transfer", Analytical Chemistry, vol. 75, No. 3, Feb. 1, 2003, 7 pages.

Petrenko et al., "Analysis and prediction of absorption band shapes, fluorescence band shapes, resonance Raman Intensities, and excitation profiles using the time-dependent theory of electronic spectroscopy", The Journal of Chemical Physics, Oct. 30, 2007, 16 pages.

Zhang et al., "Organic field-effect transistor-based gas sensors", Royal Society of Chemistry, 2015, 21 pages.

* cited by examiner

SENSOR REFRESH SYSTEMS

CROSS-REFERENCE TO RELATED APPLICATIONS

This application is a divisional application of U.S. patent application Ser. No. 16/731,430, filed Dec. 31, 2019, now U.S. Pat. No. 11/391,730 issued Jul. 19, 2022, which is incorporated by reference in its entirety herein.

TECHNICAL FIELD

The present disclosure relates to sensor systems, for example, sensor systems configured to refresh a sensor by dissociating a chemical species from a sensor of the sensor system under an optical source.

BACKGROUND

Detecting the presence of heavy metal ions in water is of great importance to enhance the quality of water. A fluorescence-based detection method has been utilized for ion (e.g., metal ions) sensing in water, where the ion attaches to a sensor to either generate or quench fluorescence. Measurement of the fluorescence can subsequently determine a concentration of the ion in water.

Refreshing a sensor permits reuse of the sensor. A binding strength between the ion and the sensor generally determines a refresh time for the sensor to return to an unbound state. The refresh time varies depending on the binding strength between the ion and the sensor.

SUMMARY

According to one embodiment, a sensor refresh system is disclosed. The sensor refresh system includes a sensor assembly including a sensing surface. The sensor refresh system includes a sensor attached to the sensing surface of the sensing assembly. The sensor includes a receptor binding a chemical species in a binding state. The sensor refresh system further includes an optical source irradiating the sensor when the chemical species is in the binding state to dissociate the chemical species from the receptor of the sensor in a dissociation state.

According to another embodiment, a sensor refresh system is disclosed. The sensor refresh system includes a sensor assembly including a sensing surface. The sensor refresh system includes a sensor attached to the sensing surface of the sensing assembly. The sensor includes a receptor binding a chemical species in a binding state. The sensor refresh system further includes a first optical source irradiating the sensor to generate fluorescence when the chemical species is in the binding state. The sensor refresh system further includes a second optical source irradiating the sensor when the chemical species is in the binding state to dissociate the chemical species from the receptor of the sensor in a dissociation state.

According to another embodiment, a sensor refresh method is disclosed. The sensor refresh method includes the step of binding a chemical species in a binding state to a receptor of a sensor attached to a sensing surface of a sensing assembly. The sensor refresh method further includes irradiating the sensor via an optical source when the chemical species is in the binding state to dissociate the chemical species from the receptor of the sensor in a dissociation state.

DETAILED DESCRIPTION

Figures 1, 2, 3, 4:
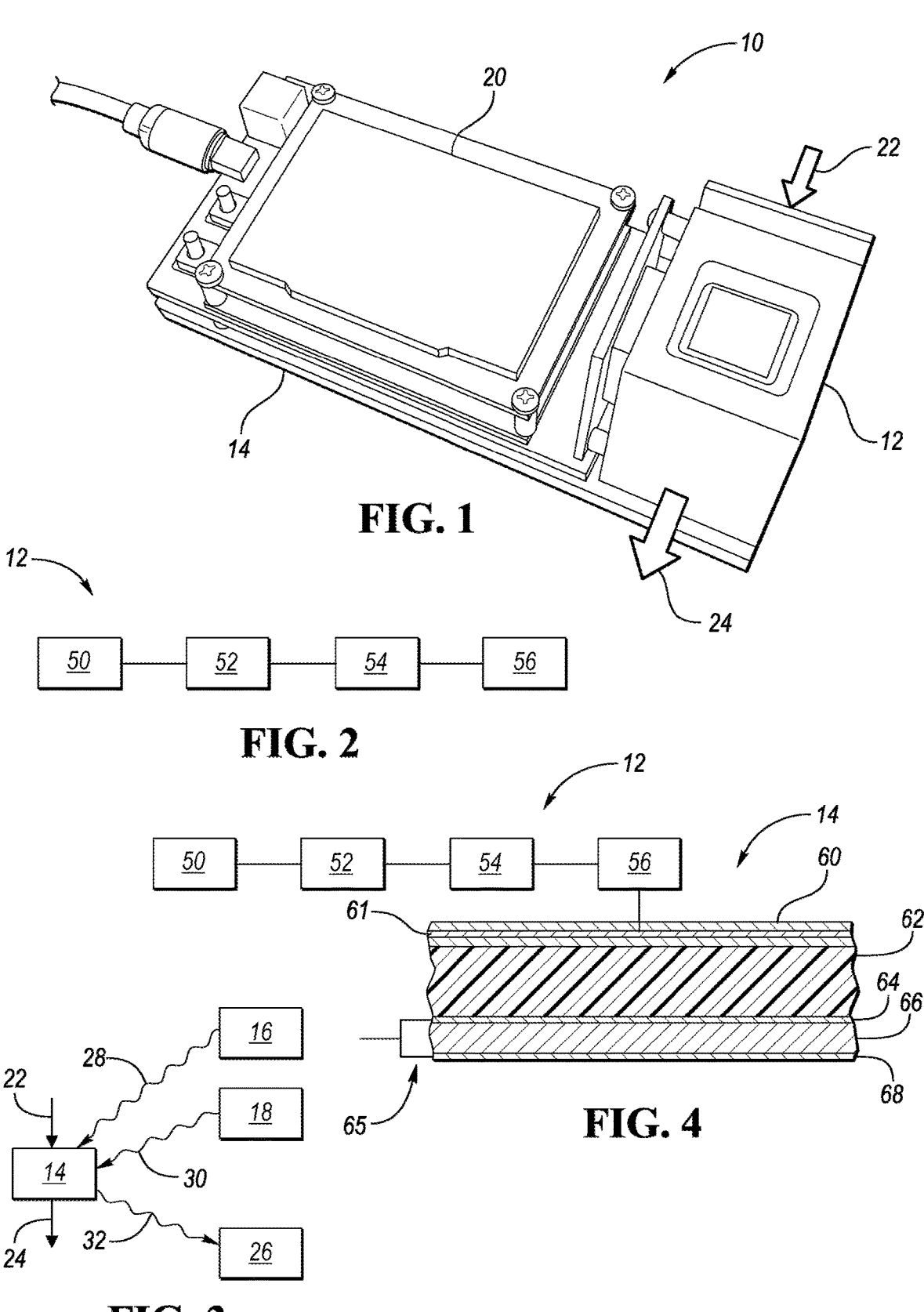
FIG. 1 depicts a schematic, perspective view of a device architecture configured to be used in a sensor system.
FIG. 2 depicts a schematic diagram of a general structural architecture of a receptor/spacer/fluorophore-type sensor configured to be used in a sensor system.
FIG. 3 depicts a schematic diagram of a device architecture described in FIG. 1 and configured to be used in a sensor system.
FIG. 4 depicts a cross-section view of a sensing assembly configured to be used in a sensor system.

Embodiments of the present disclosure are described herein. It is to be understood, however, that the disclosed embodiments are merely examples and other embodiments can take various and alternative forms. The figures are not necessarily to scale; some features could be exaggerated or minimized to show details of components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for applications or implementations.

This invention is not limited to the specific embodiments and methods described below, as specific components and/or conditions may, of course, vary. Furthermore, the terminology used herein is used only for the purpose of describing embodiments of the present invention and is not intended to be limiting in any way.

As used in the specification and the appended claims, the singular form "a," "an," and "the" comprise plural referents unless the context clearly indicates otherwise. For example, reference to a component in the singular is intended to comprise a plurality of components.

The description of a group or class of materials as suitable for a given purpose in connection with one or more embodiments implies that mixtures of any two or more of the members of the group or class are suitable. Description of constituents in chemical terms refers to the constituents at the time of addition to any combination specified in the description and does not necessarily preclude chemical interactions among constituents of the mixture once mixed.

Except where expressly indicated, all numerical quantities in this description indicating dimensions or material properties are to be understood as modified by the word "about" in describing the broadest scope of the present disclosure.

The first definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

Reference is being made in detail to compositions, embodiments, and methods of embodiments known to the inventors. However, it should be understood that disclosed embodiments are merely exemplary of the present invention which may be embodied in various and alternative forms. Therefore, specific details disclosed herein are not to be interpreted as limiting, rather merely as representative bases for teaching one skilled in the art to variously employ the present invention.

The term "substantially" or "about" may be used herein to describe disclosed or claimed embodiments. The term "substantially" or "about" may modify a value or relative characteristic disclosed or claimed in the present disclosure. In such instances, "substantially" or "about" may signify that the value or relative characteristic it modifies is within ±0%, 0.1%, 0.5%, 1%, 2%, 3%, 4%, 5%, or 10% of the value or relative characteristic.

Monitoring the quality of drinking water is important for the protection of human health. Heavy metals, such as lead (Pb), are common pollutants found in drinking water. Other heavy-metals, including arsenic (As), mercury (Hg), chromium (Cr), and cadmium (Cd), may also be found in drinking water. A fluorescence-based analyte detection technique has been utilized for detecting heavy metals in a fluid (e.g. liquid or gas) medium. One class of sensors employed by this technique is a receptor/spacer/fluorophore-type sensor. An analyte, such as an ion, binds to the sensor via the receptor of the sensor, which consequently either causes or quenches fluorescence. Measurement of the fluorescence can subsequently determine a concentration of the analyte in the fluid medium.

The bound analyte needs to be dissociated from the sensor so that the sensor may be reused. A binding strength between the analyte and the sensor generally determines a refresh time for the sensor to return to an unbound state. One technique that has been developed to refresh the sensor is by immersing the sensor in distilled water. However, because different analytes bind to the sensor with different binding strengths, a refresh time of the sensor may vary using this technique. For example, if an analyte (e.g., $Ca^{2+}$) weakly binds to the sensor, it may take thirty (30) seconds for the sensor to release the analyte into distilled water. But if an analyte strongly binds to the sensor, it may take up to forty (40) minutes for the analyte to dissociate from the sensor. Therefore, there is a need to refresh the sensor in a timelier manner for a wide range of analytes.

Aspects of the present disclosure are directed to the use of an influence, such as an optical source or an ultrasonic vibrational energy, for dissociation of an analyte from a sensor. In one embodiment, aspects of the present disclosure use infrared light, microwave, and/or radio wave as the optical source to induce photodissociation of the analyte from the sensor. In another embodiment, aspects of the present disclosure include the fabrication of at least one electroactive polymer (EAP) film in a sensing assembly of a sensor system, where the at least one EAP film deforms under the influence of an electric field, thereby generating an ultrasonic vibrational energy for dissociating the analyte from the sensor.

FIG. 1 depicts a schematic, perspective view of a device architecture of a sensor system 10. FIG. 3 depicts a schematic diagram of the device architecture of the sensor system 10. As shown in FIGS. 1 and 3, the sensor system 10 includes a sensor 12, a sensing assembly 14, a first optical source 16, a second optical source 18, an electronic screen 20, an inlet 22, and an outlet 24. The sensor 12 may be a receptor/spacer/fluorophore-type sensor or a gas sensor. When a fluid (e.g., liquid or gas) medium enters the sensor system 10 via the inlet 22, an analyte in the fluid medium binds to the sensor 12. The analyte may be an ion, including, without limitation, $Na^+$, $Mg^{2+}$, $Pb^{2+}$, $Zn^{2+}$, $As^{3+}$, $As^{5+}$, $S^{2-}$, and $F^-$, or a gas, including, without limitation, $H_2S$, NO, $NO_2$, CO, $CO_2$, $O_3$, $SO_2$, and $SO_3$, or benzothiophene, and its derivatives. The sensor system 10 optionally includes a photodetector 26, for example, a photoresistor. The photodetector 26 is configured to measure fluorescence, which may be used to determine a concentration of the analyte in the fluid medium. The electronic screen 20 displays information about the analyte, such as the concentration of the analyte in the fluid medium. In one embodiment, the displayed information on the electronic screen 20 may be transmitted to a remote device configured to monitor or record the information about the analyte. For example, the displayed information may be transmitted wirelessly or through a cable from the sensor system 10 to the remote device.

FIG. 2 depicts a schematic diagram of a general structural architecture of a receptor/spacer/fluorophore-type sensor configured to be used in a sensor system. The sensor system may be sensor system 10, and the sensor may be sensor 12. The sensor 12 is attached to a sensing surface of the sensing assembly 14 via an anchor 56. Alternatively, the sensor 12 is inserted into a film which is embedded with the sensing surface of the sensing assembly 14. In one or more embodiments, the receptor chemistry of the sensor 12 is immobilized in a polymer thin film. The polymer thin film may be a polymer matrix with a thickness. The polymer matrix may be formed of a cellulose polymer or a hydrogel. The thickness of the polymer matrix may be any of the following values or in a range of any two of the following values: 0.1, 0.5, 1, 1.5 and 2 cm. The sensor 12 further includes a receptor 50, which binds to an analyte. A spacer 52 is bound to the receptor 50, and a fluorophore 54 is bound to the spacer 52. The spacer 52 may be formed of methylamine and ethylamine. The fluorophore may be anthracene, benzene, carbazole, diphenylfurane, naphthalene, 1,8-naphthalimide, N,N,N',N'-tetramethylbenzidine, porphyrin, or pyrene.

In another embodiment, the sensor 12 may be a gas sensor. A surface of the gas sensor may contain a material configured to change electronic properties, including, without limitation, conductivity, capacitance or a redox current, upon binding to an analyte in a fluid medium. The material may be a metal oxide. A metal oxide-based surface may be configured to create a current due to a reduction or oxidation reaction that occurs upon the analyte's binding. Non-limiting examples of metal oxide receptors include tin oxide ($SnO_2$), tungsten oxide ($WO_3$), indium oxide ($In_2O_3$), zinc oxide (ZnO), combinations thereof, and optionally including dopants. The material can also be an organic semiconductor, such as pentacene, phthalocyanine, thiophene, rubrene, and optionally including dopants.

For either type of the sensor 12, continuously irradiating the sensing assembly 14 by the first optical source 16 allows the sensor 12 to selectively bind to one analyte rather than another analyte. For example, in a liquid medium containing analyte A (e.g., $Pb^{2+}$) and analyte B (e.g., $Mg^{2+}$), where the binding strength between analyte A and the sensor 12 is larger than that between analyte B and the sensor 12, a continuous irradiation (e.g., 1 to 10 minutes) of the sensing assembly 14 by the first optical source 16 allows analyte A to remain bound to the sensor 12 instead of analyte B. This selective binding of analyte A to the sensor 12 may allow an accurate measurement of the concentration of analyte A in the liquid medium.

In another embodiment, tuning the first optical source 16 to the resonance of a bond vibration or a rotation of the bond between an analyte and the sensor 12 may also allow the sensor 12 to selectively bind to one analyte rather than another analyte. For example, in a liquid medium containing analyte A (e.g., $Pb^{2+}$) and analyte B (e.g., $Mg^{2+}$), selectively tuning the first optical source 16 to the resonance of the bond between analyte B and the sensor 12 may weaken the bond such that analyte B would be dissociated from the sensor 12 under the influence of the first optical source 16, whereas analyte A may remain bound to the sensor 12.

FIG. 3 depicts a schematic diagram of the device architecture described in FIG. 1 and configured to be used in the sensor system 10. The first optical source 16 of the sensor system 10 directs light, for example, visible light, shown by first arrow 28, onto the sensing assembly 14 while a fluid (e.g., liquid or gas) medium is flowing through the sensor system 10. In one embodiment, when the sensor 12 is the receptor/spacer/fluorophore-type sensor shown in FIG. 2, the binding of an analyte in the fluid medium to the sensor 12 may generate fluorescence, shown by third arrow 32, which can be subsequently measured by the photodetector 26 for determining the concentration of the analyte. In another embodiment, when the sensor 12 is a gas sensor, the binding of the analyte in the fluid medium to the sensor 12 may cause changes to electronic properties, including, without limitation, conductivity, capacitance or a redox current, of a surface of the gas sensor. Measurement of the changes may indicate the concentration of the analyte in the fluid medium.

In FIGS. 1 and 3, the first optical source 16 may be configured to generate a first optical signal having a first wavelength. The first wavelength may be selected based on the energy required to generate fluorescence when an analyte in a fluid medium binds to the sensor 12. The second optical source 18 may be configured to generate a second optical signal having a second wavelength. The second wavelength may be selected based on a frequency required to assist dissociation of the analyte in the fluid medium from the sensor 12.

In one embodiment, the second wavelength may be different from the first wavelength. For example, the second wavelength may be in a range from 1 μm to 1 mm, and the first wavelength may be in a range from 380 nm to 700 nm. In another embodiment, the first and the second wavelengths may be within a similar range. In yet another embodiment, the first and the second optical sources 16 and 18 may be combined as a single optical source, where irradiating the sensing assembly 14 during a first time-range (e.g., <1 min) may generate fluorescence due to the binding of the analyte to the sensor 12 and irradiating the sensing assembly 14 for a longer period (e.g. 5 to 10 mins) may allow the sensor 12 to release the bound analyte into the fluid medium.

The structure of fluorophore 54 of the receptor/space/ fluorophore-type sensor 12 shown in FIG. 2 may also have an influence in the selection of the first optical source 16. For example, if the fluorophore 54 is 1,8-naphthalimide, the first wavelength generated by the first optical source 16 can be around 450 nm, and the resulting fluorescence due to the binding of an analyte to the sensor 12 may be around 550 nm.

To refresh the sensor 12 after an analyte detection event, the sensor system 10 may be configured to discontinue the direction of light from the first optical source 16 and start the direction of light from the second optical source 18. The second optical source 18 may be infrared light, microwave, and/or radio wave. As a result, irradiation by the second optical source 18 onto the sensing assembly 14 induces photodissociation of the analyte from the sensor 12, thereby resetting the sensor 12 to an unbound state. The second optical source 18 may be configured to be tuned to the resonance of a bond vibration or a rotation of the bond between an analyte and the receptor 50 allowing for an efficient dissociation of the analyte from the sensor 12. The sensor system 10 may be configured to at least partially dry the receptor before turning on the second optical source 18.

In one embodiment, since the absorption of water in the near infrared range (e.g., when using the second optical source 18) is significantly higher than that in the visible light range (e.g., when using the first optical source 16), irradiation of the sensing assembly 14 by the second optical source 18 may heat the water, which may consequently accelerate aging or degradation of the sensing assembly 14. Therefore, to prevent the aging or degradation, the sensing assembly 14 may be completely or partially dried before starting the direction of light from the second optical source 18 for refreshing the sensor 12.

FIG. 4 depicts a cross-section view of a sensing assembly 14 of the sensor system 10 according to an embodiment. The sensing assembly 14 includes a sensing surface 60, a first electrode 64, a second electrode 68, a polymer support layer 62 positioned between the sensing surface 60 and the first electrode 64, and at least one electroactive polymer (EAP) film 66 positioned between the first and the second electrodes 64, and 68. FIG. 4 depicts sensor 12 attached to sensing surface 60 of sensing assembly 14. As shown in FIG. 4, sensing assembly 14 includes polymer thin film 61 embedded with sensing surface 60 to immobilize sensor 12 on sensing surface 60.

The at least one EAP film 66 may be formed of as an EAP material configured to undergo a change in its size or shape under the influence of an electric field. The EAP material may be hydrophobic to allow the at least one EAP film 66 to work in an aqueous environment. In one or more embodiments, the sensing assembly 14 may also include a circuit 65 in an electrical communication with the first and the second electrodes 64 and 68. The circuit may be configured to provide an electrical signal to the at least one of the first and the second electrodes 64 and 68 to generate an electric field that causes the at least one EAP film 66 to deform. The deformation of the at least one EAP film 66 produces an ultrasonic vibrational energy which transmits from the at least one EAP film 66 to the sensing surface 60. The ultrasonic vibrational energy then causes the bound analyte to be released from the sensor 12, thereby refreshing the sensor 12.

The sensing assembly 14 may be fabricated using a screen-printing technique, which allows the at least one EAP film 66 to be in contact with the first and the second electrodes 64 and 68. In one or more embodiments, a thickness of each of the first and the second electrodes 64 and 68 may be between 100 nm and 1 μm. In one or more embodiments, a thickness of the at least one EAP film 66 is between 10 μm and 100 μm. The thickness and a crystalline structure of the at least one EAP film 66 may also be tuned to provide a resonance frequency of vibration that allows for an efficient dissociation of the analyte from the sensor 12. In one embodiment, the first and the second electrodes 64 and 68 are hydrophobic electrodes.

While the sensor systems disclosed herein may be utilized as part of a sensor system for water quality, the disclosed sensor systems may be used as parts of other systems as well. Non-limiting examples of other systems include a sensor to measure the components of blood, a sensor to measure the components of a cell, a hot water tank for a thermal heating system, and/or a fuel tank for automotive or aerospace applications.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for applications.

What is claimed is:

1. A sensor refresh method comprising:

binding a chemical species in a binding state to a receptor of a sensor attached to a sensing surface of a sensor assembly to detect the chemical species;

tuning an optical source to a resonant frequency of a bond vibration or a rotation of the receptor and the chemical species in the binding state; and irradiating the sensor via the optical source at the resonant frequency when the chemical species is in the binding state to dissociate the chemical species from the receptor of the sensor in a dissociation state.

2. The sensor refresh method of claim 1, wherein the chemical species is a gas.

3. The sensor refresh method of claim 1, wherein the sensor includes a spacer bound to the receptor, a fluorophore bound to the spacer, and an anchor bound to the fluorophore and attaching the sensor to the sensing surface of the sensing assembly.

4. The sensor refresh method of claim 3, wherein the sensor includes a photodetector determining an amount of the chemical species by measuring fluorescence when the optical source irradiates the sensor when the chemical species is in the binding state.

5. The sensor refresh method of claim 3, wherein the fluorophore is carbazole, diphenylfurane, naphthalene, N,N, N',N'-tetramethylbenzidine, or porphyrin.

6. The sensor refresh method of claim 1, wherein the sensing surface has a material undergoing one or more electronic property changes upon binding to the chemical species.

7. The sensor refresh method of claim 6, wherein the material is a metal oxide or an organic semiconductor.

8. The sensor refresh method of claim 1, wherein the sensing assembly further comprises a polymer thin film embedded with the sensing surface to immobilize the sensor on the sensing surface thereof.

9. A sensor refresh method comprising:

binding a chemical species in a binding state to a receptor of a sensor attached to a sensing surface of a sensing assembly to detect the chemical species;

tuning an optical source to a resonant frequency of a bond vibration or a rotation of the receptor and the chemical species in the binding state;

after detecting the chemical species, completely or at least partially drying the receptor; and after the drying step, irradiating the sensor via the optical source at the resonant frequency when the chemical species is in the binding state to dissociate the chemical species from the receptor of the sensor in a dissociation state.

10. The sensor refresh method of claim 9, wherein the chemical species is a gas.

11. The sensor refresh method of claim 9, wherein the sensor includes a spacer bound to the receptor, a fluorophore bound to the spacer, and an anchor bound to the fluorophore and attaching the sensor to the sensing surface of the sensing assembly.

12. The sensor refresh method of claim 11, wherein the sensor includes a photodetector determining an amount of the chemical species by measuring fluorescence when the optical source irradiates the sensor when the chemical species is in the binding state.

13. The sensor refresh method of claim 12, wherein the fluorophore is carbazole, diphenylfurane, naphthalene, N,N, N',N'-tetramethylbenzidine, or porphyrin.

14. The sensor refresh method of claim 13, wherein the fluorophore is carbazole.

15. The sensor refresh method of claim 13, wherein the fluorophore is diphenylfurane.

16. The sensor refresh method of claim 13, wherein the fluorophore is naphthalene.

17. The sensor refresh method of claim 13, wherein the fluorophore is N,N,N',N'-tetramethylbenzidine.

18. The sensor refresh method of claim 13, wherein the fluorophore is porphyrin.

19. The sensor refresh method of claim 9, wherein the tuning step includes tuning the optical source to the resonant frequency of the bond vibration of the receptor and the chemical species in the binding state.

20. The sensor refresh method of claim 9, wherein the tuning step includes tuning the optical source to the resonant frequency of the rotation of the receptor and the chemical species in the binding state.

* * * * *